(12) United States Patent
Ralph

(10) Patent No.: US 8,356,609 B1
(45) Date of Patent: Jan. 22, 2013

(54) PLAQUE BUSTER SYSTEM

(76) Inventor: Clemon W. Ralph, Tampa, FL (US)

( * ) Notice: Subject to any disclaimer, the term of this patent is extended or adjusted under 35 U.S.C. 154(b) by 232 days.

(21) Appl. No.: 12/799,302

(22) Filed: Apr. 22, 2010

(51) Int. Cl.
*A45D 44/18* (2006.01)
*A61K 8/00* (2006.01)

(52) U.S. Cl. .......................................... 132/308; 424/53

(58) Field of Classification Search .......... 132/308–311; 206/572; 424/53
See application file for complete search history.

(56) References Cited

U.S. PATENT DOCUMENTS

| | | | | |
|---|---|---|---|---|
| 1,962,337 A | * | 6/1934 | Youngstrom | 132/308 |
| 2,223,952 A | * | 12/1940 | Darmody | 132/308 |
| D335,256 S | * | 5/1993 | Slavin et al. | D9/724 |
| 5,634,792 A | * | 6/1997 | Brisendine | 433/180 |
| 5,660,546 A | * | 8/1997 | Shafer | 433/216 |
| 6,116,426 A | * | 9/2000 | Slonim | 206/570 |
| 6,206,192 B1 | * | 3/2001 | Winstead et al. | 206/572 |
| 6,254,294 B1 | * | 7/2001 | Muhar | 401/26 |
| 6,645,472 B1 | * | 11/2003 | Anderson | 424/53 |
| 2011/0036746 A1 | * | 2/2011 | Bear | 206/572 |

* cited by examiner

*Primary Examiner* — Robyn Doan

(57) ABSTRACT

A plaque buster system is for removing stains and whitening both teeth and dentures and for tongue cleaning and mouth washing. A composition in a dry power form consists of baking soda plus vitamin C/ascorbic acid plus ground peppermint. A container/dispenser receives and dispenses the composition.

5 Claims, 2 Drawing Sheets

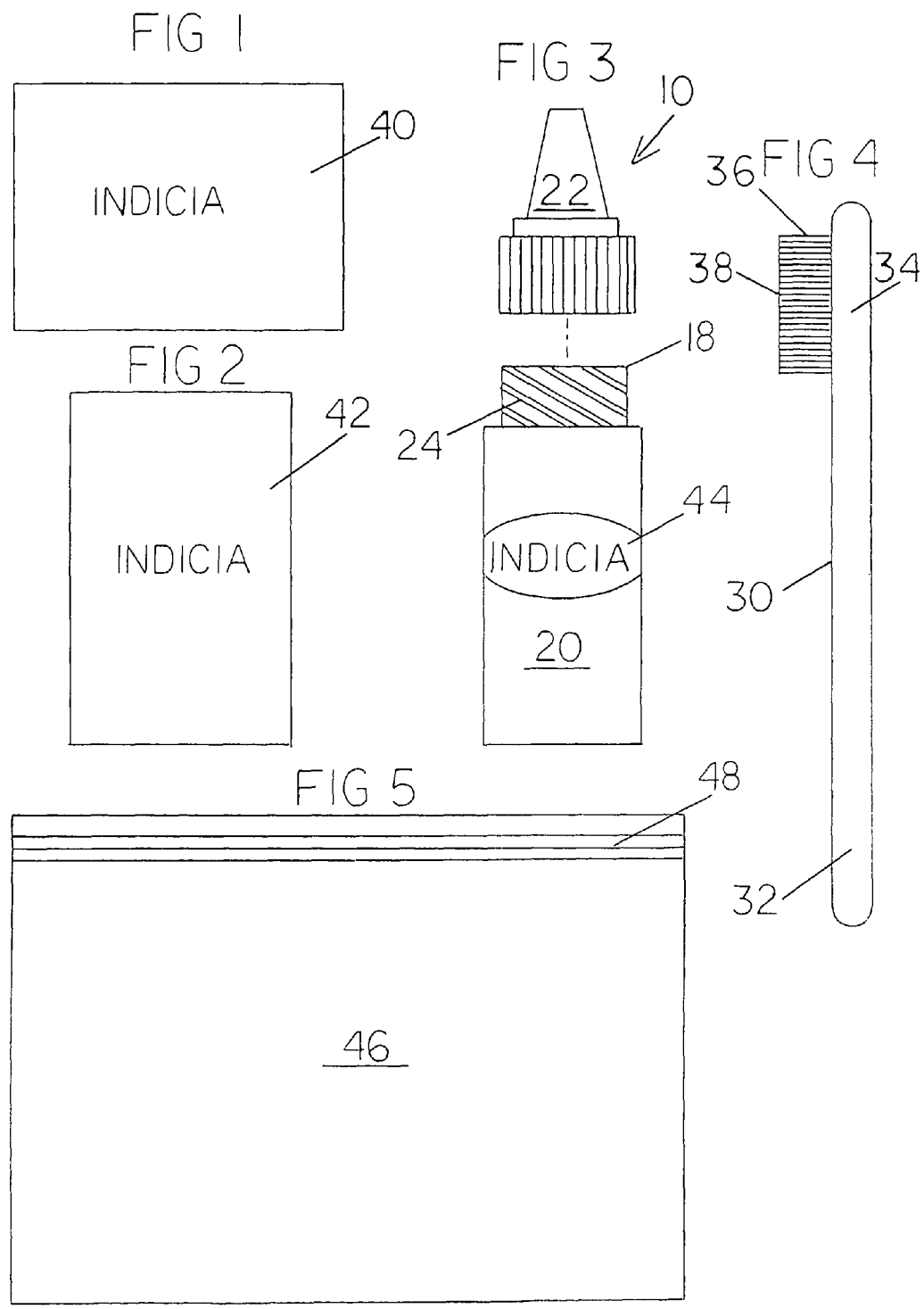

PLAQUE BUSTER SYSTEM

BACKGROUND OF THE INVENTION

1. Field of the Invention

The present invention relates to a plaque buster system and more particularly pertains to removing stains and whitening both teeth and dentures and for tongue cleaning and mouth washing, all in a safe, ecological, clean, economical manner.

2. Description of the Prior Art

The use of dental hygiene systems of known designs and configurations is known in the prior art. More specifically, dental hygiene systems of known designs and configurations previously devised and utilized for the purpose of cleaning teeth and dentures and the tongue and for mouth washing are known to consist basically of familiar, expected, and obvious structural configurations, notwithstanding the myriad of designs encompassed by the crowded prior art which has been developed for the fulfillment of countless objectives and requirements.

While these prior art devices fulfill their respective, particular objectives and requirements, the aforementioned patents do not describe a plaque buster system that allows removing stains and whitening both teeth and dentures and for tongue cleaning and mouth washing, all in a safe, ecological, clean, economical manner.

In this respect, the plaque buster system according to the present invention substantially departs from the conventional concepts and designs of the prior art, and in doing so provides an apparatus primarily developed for the purpose of removing stains and whitening both teeth and dentures and for tongue cleaning and mouth washing, all in a safe, ecological, clean, economical manner.

Therefore, it can be appreciated that there exists a continuing need for a new and improved plaque buster system which can be used for removing stains and whitening both teeth and dentures and for tongue cleaning and mouth washing, all in a safe, ecological, clean, economical manner. In this regard, the present invention substantially fulfills this need.

SUMMARY OF THE INVENTION

In view of the disadvantages inherent in the types of dental hygiene systems of known designs and configurations now present in the prior art, the present invention provides an improved plaque buster system. As such, the general purpose of the present invention, which will be described subsequently in greater detail, is to provide a new and improved plaque buster system and method which has all the advantages of the prior art and none of the disadvantages.

To attain this, the present invention essentially comprises a composition in dry powder form. The composition consists of 6 parts baking soda plus 2 parts vitamin C/ascorbic acid plus 1 part ground peppermint.

A container/dispenser is provided. The container/dispenser has a lower component. The container/dispenser has an upper component. The lower component has a cylindrical side wall. The lower component has a closed bottom. The lower component has an open top. Male screw threads are provided. The male screw threads are provided adjacent to the open top. The upper component is provided in a frusto-conical configuration. A passageway is provided through the upper component. The upper component has female screw threads. In this manner the upper component may be coupled and uncoupled to the lower component. The upper component is fabricated of a relatively rigid plastic material. The lower component is fabricated of a flexible, resilient plastic material. The container/dispenser receives the composition. In this manner when the lower component is squeezed and deformed, a quantity of composition is dispensed through the passageway in a dry cloud form.

Provided next is a toothbrush. The toothbrush has a handle end. The toothbrush has a brushing end. The toothbrush has a plurality of bristles. The bristles extend perpendicularly from the brushing end. All of the plurality of the bristles have tips. All of the tips are located in a common plane. The bristles are adapted to be moistened with water and a quantity of composition dispensed thereon.

Further provided is a plurality of sheets. The sheets include a first sheet. The first sheet has content information relating to the content of the composition. The plurality of sheets include a second sheet. The second sheet includes use information. The use information relates to use of the composition. The plurality of sheets include labeling information on the container/dispenser.

Provided last is a bag fabricated of a flexible, transparent plastic material. The bag has a slidable closure adapted to open and close the bag. The bag is adapted to receive and removably support the container/dispenser with the composition, the toothbrush and the first and second sheets.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the invention be regarded as including such equivalent constructions insofar as they do not depart from the spirit and scope of the present invention.

It is, therefore, an object of the present invention to provide a new and improved plaque buster system which has all of the advantages of the prior art dental hygiene systems of known designs and configurations and none of the disadvantages.

It is another object of the present invention to provide a new and improved plaque buster system which may be easily and efficiently manufactured and marketed.

It is further object of the present invention to provide a new and improved plaque buster system which is of durable and reliable constructions.

An even further object of the present invention is to provide a new and improved plaque buster system which is susceptible of a low cost of manufacture with regard to both materials and labor, and which accordingly is then susceptible of low prices of sale to the consuming public, thereby making such plaque buster system economically available to the buying public.

Even still another object of the present invention is to provide a plaque buster system for removing stains and whitening both teeth and dentures and for tongue cleaning and mouth washing, all in a safe, ecological, clean, economical manner.

Lastly, it is an object of the present invention to provide a new and improved plaque buster system for removing stains and whitening both teeth and dentures and for tongue cleaning and mouth washing. A composition in a dry power form consists of baking soda plus vitamin C/ascorbic acid plus ground peppermint. A container/dispenser receives and dispenses the composition.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIGS. 1 and 2 are indicia sheets, part of the plaque buster system constructed in accordance with the principles of the present invention.

FIG. 3 is an exploded view of a container/dispenser constructed in accordance with the principles of the present invention.

FIG. 4 is a front elevational view of a toothbrush constructed in accordance with the principles of the present invention.

FIG. 5 is a front elevational view of a bag constructed in accordance with the principles of the present invention.

The same reference numerals refer to the same parts throughout the various Figures.

DESCRIPTION OF THE PREFERRED EMBODIMENT

Figure 6:
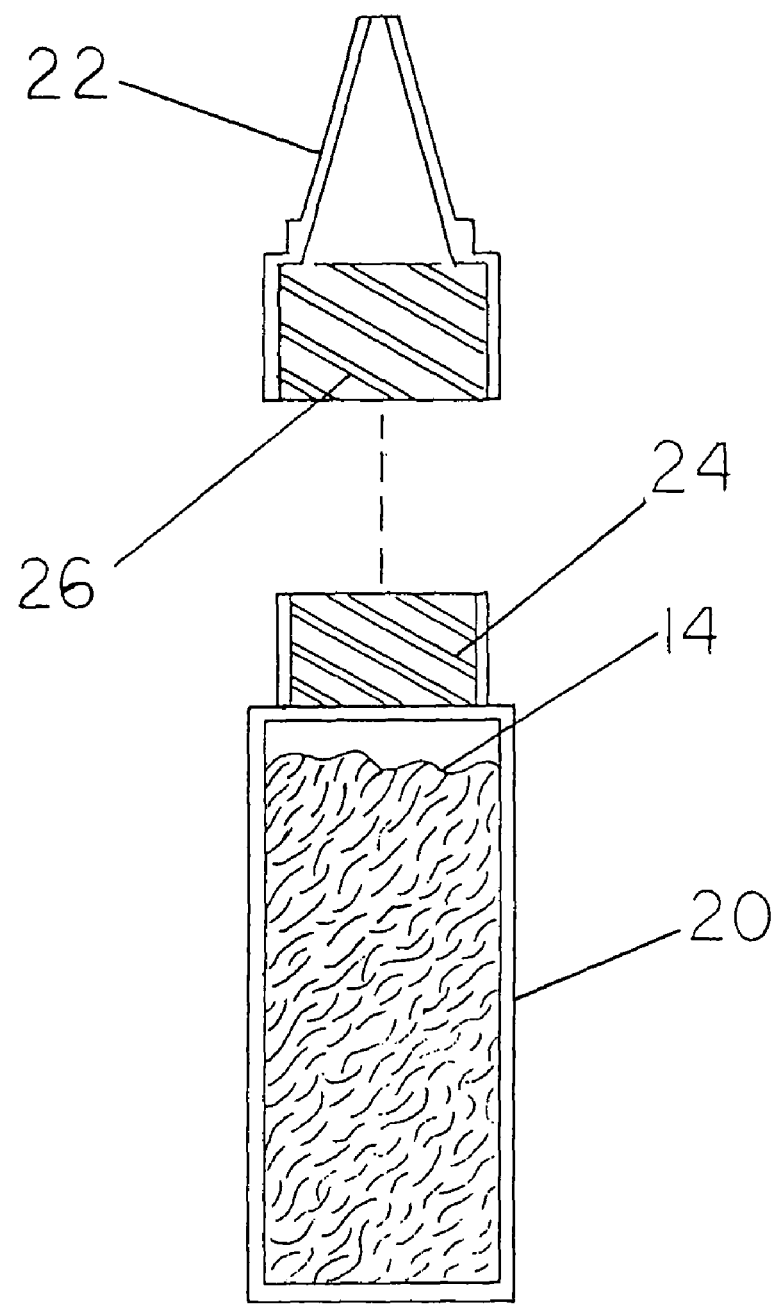
FIG. 6 is an exploded view, partly in cross section, of a container/dispenser constructed in accordance with the principles of the present invention.

With reference now to the drawings, and in particular to FIG. 1 thereof, the preferred embodiment of the new and improved plaque buster system embodying the principles and concepts of the present invention and generally designated by the reference numeral 10 will be described.

The present invention, the plaque buster system 10 is comprised of a plurality of components. Such components are individually configured and correlated with respect to each other so as to attain the desired objective. In their broadest context such include a composition consisting of baking soda plus vitamin C/ascorbic acid plus ground peppermint and a container/dispenser. In this broad context, the composition consists of baking soda plus vitamin C/ascorbic acid plus ground peppermint. The composition is provided in dry powder form. A container/dispenser is provided. The container/dispenser receives and dispenses the composition. Such components are individually configured and correlated with respect to each other so as to attain the desired objective.

In the preferred embodiment of the plaque buster system, designated by reference numeral 10. First provided is a composition 14. The composition consists of 6 parts baking soda plus 2 parts vitamin C/ascorbic acid plus 1 part ground peppermint. The composition is provided in dry powder form.

A container/dispenser 18 is provided. The container/dispenser has a lower component 20. The container/dispenser has an upper component 22. The lower component has a cylindrical side wall. The lower component has a closed bottom. The lower component has an open top. Male screw threads 24 are provided. The male screw threads are provided adjacent to the open top. The upper component is provided in a frusto-conical configuration. A passageway is provided through the upper component. The upper component has female screw threads 26. In this manner the upper component may be coupled and uncoupled to the lower component. The upper component is fabricated of a relatively rigid plastic material. The lower component is fabricated of a flexible, resilient plastic material. The container/dispenser receives the composition. In this manner when the lower component is squeezed and deformed, a quantity of composition is dispensed through the passageway in a dry cloud form.

Provided next is a toothbrush 30. The toothbrush has a handle end 32. The toothbrush has a brushing end 34. The toothbrush has a plurality of bristles 36. The bristles extend perpendicularly from the brushing end. All of the plurality of the bristles have tips 38. All of the tips are located in a common plane. The bristles are adapted to be moistened with water and a quantity of composition dispensed thereon.

Further provided is a plurality of sheets. The sheets include a first sheet 40. The first sheet has content information relating to the content of the composition. The content of the composition includes Vitamin C—calcium ascorbic, whitener—sodium acid pyrophosphate, monocalcium phosphate, sodium bicarbonate, Gluten—aluminum free, white corn starch preservative, total fats 0 g, saturated Fat 0 g, % trans fats 0 g, % Cholesterol, and 0 m sodium 100, made by the Awesome Bright Health Product Co., Tampa, Fla. 33605.

The plurality of sheets include a second sheet 42. The second sheet includes use information. The use information relates to use of the composition. The use of the composition includes Plaque Buster—Ultra Oral Hygiene, 4 in 1 cleaning system—1. removes tartar, stains from teeth, denture, 2. a whitener, 3. a mouth wash, removes germ plaque causing odor leaving natural clean taste, 4, a tongue cleaner, direction: put dispenser cap on container and open hole at end of spout then moisten tooth brush with water, sparingly put 2 dashes of plague buster powder on tooth brush, begin brushing op row teeth for 1 or 2 minutes, same application for bottom row teeth, then rinse, moisture will activate ingredients, the more you precede with application the better oral hygiene results, it is safe and effective, will not harm you, for mouth wash—fill the cap with "P.B." pour into cup 2 oz of water, mix, gargle all as long as possible, dispense, then drink the rest it all good, results "Bam the Bomb" freshness. Product of "awesome Bright Health Co." Patent Pending,—Keep dry at all time.

The plurality of sheets include labeling information 44 on the container/dispenser. The labeling information includes Plaque Buster, a revolutionary complete 4-in-1 system, this amazing product removes tartar and stains from teeth and dentures, it's a whitener, a mouthwash, germ & odor remover and tongue cleaner—all in one, leaves a naturally clean taste, a product of Awesome Bright Health Company, Tampa, Fla., Office (813) 242-8712, Cell (813) 918-5974, ask for Ralph.

Provided last is a bag 46. The bag is fabricated of a flexible, transparent plastic material. The bag has a slidable closure 48. The closure is adapted to open and close the bag. The bag is adapted to receive and removably support the container/dispenser with the composition, the toothbrush and the first and second sheets.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact

What is claimed as being new and desired to be protected by Letters Patent of the United States is as follows:

1. A plaque buster system for removing stains and whitening both teeth and dentures and for tongue cleaning and mouth washing, all in a safe, ecological, clean, economical manner, the system comprising, in combination:

a composition consisting of 6 parts baking soda plus 2 parts vitamin C/ascorbic acid plus 1 part ground peppermint, the composition being in dry powder form; and a container/dispenser for receiving and dispensing the composition, the container/dispenser including a lower component and an upper component, the lower component having a cylindrical side wall and a closed bottom and an open top, male screw threads adjacent to the open top, the upper component being in a frusto-conical configuration with a passageway there through, the upper component having female screw threads for coupling and uncoupling the upper component and the lower component, the upper component being fabricated of a relatively rigid plastic material, the lower component being fabricated of a flexible, resilient plastic material, the container/dispenser receiving the composition whereby when the lower component is squeezed and deformed, a quantity of composition is dispensed through the passageway in a dry cloud form.

2. The system as set forth in claim 1 and further including:
a toothbrush having a handle end and a brushing end, a plurality of bristles extending perpendicularly from the brushing end, all of the plurality of the bristles having tips and all of the tips being located in a common plane, the bristles adapted to be moistened with water and a quantity of composition dispensed thereon.

3. The system as set forth in claim 2 and further including:
a plurality of sheets including a first sheet and a second sheet, the first sheet having content information relating to the content of the composition, the second sheet having use information relating to use of the composition.

4. The system as set forth in claim 3 and further including:
a bag fabricated of a flexible, transparent plastic material, the bag having a slidable closure adapted to open and close the bag, the bag adapted to receive and removably support the container/dispenser with composition, the toothbrush and the first and second sheets.

5. A natural anti-biotic plaque buster system (10) for removing stains and whitening both teeth and dentures and for tongue cleaning and mouth washing, all in a safe, ecological, clean, economical manner, the system comprising, in combination:

a composition (14) consisting of 6 parts baking soda plus 2 parts vitamin C/ascorbic acid plus 1 part ground peppermint, the composition being in dry powder form;

a container/dispenser (18) having a lower component (20) and an upper component (22), the lower component having a cylindrical side wall and a closed bottom and an open top, male screw threads (24) adjacent to the open top, the upper component being in a frusto-conical configuration with a passageway there through, the upper component having female screw threads (26) for coupling and uncoupling the upper component and the lower component, the upper component being fabricated of a relatively rigid plastic material, the lower component being fabricated of a flexible, resilient plastic material, the container/dispenser receiving the composition whereby when the lower component is squeezed and deformed, a quantity of composition is dispensed through the passageway in a dry cloud form;

a toothbrush (30) having a handle end (32) and a brushing end (34), a plurality of bristles (36) extending perpendicularly from the brushing end, all of the plurality of the bristles having tips (38) and all of the tips being located in a common plane, the bristles adapted to be moistened with water and a quantity of composition dispensed thereon;

a plurality of sheets including a first sheet (40) having content information relating to the content of the composition including Vitamin C—calcium ascorbic, whitener—sodium acid pyrophosphate, monocalcium phosphate, sodium bicarbonate, Gluten—aluminum free, white corn starch preservative, total fats 0 g, saturated Fat 0 g, % trans fats 0 g, % Cholesterol, 0 m sodium 100, made by the Awesome Bright Health Product Co., Tampa, Fla. 33605;

the plurality of sheets including a second sheet (42) having use information relating to use of the composition including Plaque Buster—Ultra Oral Hygiene, 4 in 1 cleaning system—1. removes tartar, stains from teeth, denture, 2. a whitener, 3. a mouth wash, removes germ plaque causing odor leaving natural clean taste, 4, a tongue cleaner, direction: put dispenser cap on container and open hole at end of spout then moisten tooth brush with water, sparingly put 2 dashes of plague buster powder on tooth brush, begin brushing op row teeth for 1 or 2 minutes, same application for bottom row teeth, then rinse, moisture will activate ingredients, the more you precede with application the better oral hygiene results, it is safe and effective, will not harm you, for mouth wash—fill the cap with "P.B." pour into cup 2 oz of water, mix, gargle all as long as possible, dispense, then drink the rest it all good, results "Bam the Bomb" freshness. Product of "awesome Bright Health Co." Patent Pending,—Keep dry at all time;

the plurality of sheets including labeling information (44) on the container/dispenser; Plaque Buster, a revolutionary complete 4-in -1 system, this amazing product removes tartar and stains from teeth and dentures, it's a whitener, a mouthwash, germ & odor remover and tongue cleaner—all in one, leaves a naturally clean taste, a product of Awesome Bright Health Company, Tampa, Fla., Office (813) 242-8712, Cell (813) 918-5974, ask for Ralph; and a bag (46) fabricated of a flexible, transparent plastic material, the bag having a slidable closure (48) adapted to open and close the bag, the bag adapted to receive and removably support the container/dispenser with the composition, the toothbrush and the first and second sheets.

* * * * *